United States Patent
Boesen et al.

(10) Patent No.: US 11,759,419 B2
(45) Date of Patent: Sep. 19, 2023

(54) COMPRESSED NICOTINE LOZENGE

(71) Applicant: Fertin Pharma A/S, Vejle (DK)

(72) Inventors: Dorthe Schackinger Boesen, Vejle (DK); Heidi Ziegler Bruun, Vejle Øst (DK); Bruno Provstgaard Nielsen, Vejle Øst (DK); Kent Albin Nielsen, Brande (DK); Rikke Pranger-Rasmussen, Vejle (DK)

(73) Assignee: Fertin Pharma A/S, Vejle (DK)

( * ) Notice: Subject to any disclaimer, the term of this patent is extended or adjusted under 35 U.S.C. 154(b) by 85 days.

(21) Appl. No.: 16/599,629

(22) Filed: Oct. 11, 2019

(65) Prior Publication Data

US 2021/0106521 A1  Apr. 15, 2021

(51) Int. Cl.
*A61K 9/00* (2006.01)
*A61K 31/465* (2006.01)
*A61K 47/26* (2006.01)
*A61K 47/32* (2006.01)

(52) U.S. Cl.
CPC .......... *A61K 9/0056* (2013.01); *A61K 31/465* (2013.01); *A61K 47/26* (2013.01); *A61K 47/32* (2013.01)

(58) Field of Classification Search
None
See application file for complete search history.

(56) References Cited

U.S. PATENT DOCUMENTS

| 2011/0110880 A1* | 5/2011 | Chen .................... A61K 9/2027 424/78.15 |
| 2018/0140591 A1 | 5/2018 | Wittorff et al. |
| 2018/0333354 A1 | 11/2018 | McNally et al. |

FOREIGN PATENT DOCUMENTS

| WO | WO2010/044736 | * | 4/2010 |
| WO | WO2010121619 A1 | | 10/2010 |

OTHER PUBLICATIONS

International Search Report dated Jun. 24, 2020 in International Application No. PCT/DK2020/050103, 5 pages.

* cited by examiner

*Primary Examiner* — Patricia Duffy
*Assistant Examiner* — Garen Gotfredson
(74) *Attorney, Agent, or Firm* — Lee & Hayes, P.C.

(57) ABSTRACT

A water-dissolvable compressed oral nicotine lozenge is disclosed, the oral nicotine lozenge comprising a first module and a second module, the first and the second modules being fused by compression, the first module being a lozenge module comprising at least one sugar alcohol and the second module being an FDT-module comprising at least one sugar alcohol and nicotine. Also, a method of manufacturing a water-dissolvable compressed oral nicotine lozenge is disclosed.

18 Claims, No Drawings

COMPRESSED NICOTINE LOZENGE

FIELD OF THE INVENTION

The invention relates to a compressed nicotine lozenge and the method of making a compressed nicotine lozenge.

BACKGROUND OF THE INVENTION

Different kinds of delivery vehicles have been applied for oral administration of nicotine to users. Such delivery vehicles include pouches, chewing gum and lozenges. General expectations from the users are that relief from nicotine craving is obtained at the right time, while still experiencing pleasure during administration of the nicotine.

It is however a significant challenge within the technical area to address what the users really want with respect to user experience. What is important in relation to the effect of the nicotine in relation of craving and what is important parameters in relation to taste and user of the delivery vehicles and even more important, what is the most acceptable tradeoffs between the different reaction- and experience chains during use of the delivery vehicle.

These tradeoffs have been an ongoing challenge for the relevant industry during many years.

The present invention addressed the challenges and tradeoffs particularly related to users expectations related to nicotine delivery vehicles when comparing to what a user may experience when e.g. smoking a cigarette.

SUMMARY

The invention relates to a water-dissolvable compressed oral nicotine lozenge comprising a first module and a second module, the first and the second modules being fused by compression, the first module being a lozenge module comprising at least one sugar alcohol and the second module being an FDT-module comprising at least one sugar alcohol and nicotine.

In the present context a module is defined as a plurality of a compressed particles. A typical implementation of such a lozenge would e.g. be a lozenge consisting of two modules, a first and a second module, and where each module is a layer of the lozenge. In other words, such an example would be a two-layer lozenge. Other number of modules may be applied within the scope of the invention.

It should be noted that the understanding of a module in the present context is a module enabling and facilitating the intended effect, i.e. an effective delivery or administration of nicotine and at the same time providing the intended masking. This imposes some structural restrictions on the modules in the sense that modules must be large enough to be able to not only deliver the nicotine but also the desired masking compounds, and at the right time.

A module in the present context thus, in an advantageous embodiment, encompasses a population of compressed particles weighing at least 10% by weight of the lozenge. In other words, a module is not intended to refer to individual particles as conventionally understood from the art of tableting.

In terms of the first module being a lozenge, a lozenge is a well-known term in relation to medicated tablets intended to be dissolved or disintegrated slowly in the mouth, typically to release an active ingredient. Lozenges with different active ingredients are known, e.g. nicotine lozenges and lozenges for temporarily stopping e.g. coughs and lubricate and soothe irritated tissues of the throat (usually due to a sore throat).

The second module is designed and provided as a module which in itself is characterized by being an FDT, i.e. a module having the characteristics of a so-called fast disintegrating tablet. Fast disintegrating tablets generally exhibits fast disintegration, typically below 60 seconds from placing it in the mouth, or even faster such as 30 seconds from placing it in the mouth.

The idea of combining two structurally differently designed modules, one module containing nicotine, makes it possible to provide a nicotine delivering lozenge where taste masking and pleasure is combined with an impressive effect to a user.

The second module is typically designed to disintegrate in less than 60 seconds upon oral administration in the multi-module lozenge.

It is however surprising that the desired effect is obtained by masking by the first module, but at the same time keeping the concentration of nicotine in the FDT under a certain level. The desired effect may e.g. include nicotine craving relief, taste and/or pleasure as perceived by the user.

Fast dissolving tablets represent an ideal way of providing the nicotine user with a fast dose/burst of nicotine giving fast effect. However, this fast craving relief does not fully cover the pleasure often associated with desired pleasure for the nicotine user. Also, undesired side effects may occur in case of too high nicotine load delivered too fast.

A prolonged pleasure sensation may thus be obtained by merging the fast craving relief sensation with a second phase sensation into one lozenge.

Compression/fusion of two such different composition into a single multi-modular lozenge may not necessarily be trivial as the invention requires a certain design to get the desired effect.

The invention, among many advantages, benefits from an intuitive and fool-proof use of nicotine as compared to prior art delivery vehicles.

User time may be easily designed to by around 5 minutes, i.e. similar to smoking a cigarette. The bitter taste of nicotine may be reduced.

In an advantageous embodiment of the invention the first module provides suitable long-term masking of the nicotine and at the same time the second module provides a very fast release of nicotine at a concentration preferably at a level which is below a certain level, thereby ensuring that the initial burning is masked the best way possible.

The use of a module FDT in a lozenge applied as nicotine release vehicle furthermore facilitates the manufacture of robust tablets, providing a prolonged release of masking compounds while at the same time prolonging an invoked salivation during use of the tablet.

In an advantageous embodiment the second module comprises nicotine in an amount of less than 5% by weight of the second module, such as less than 3% by weight of the second module, such as less than 2% by weight of the second module.

In an embodiment of the invention the second module comprises nicotine in an amount of 0.2 to 5% by weight of the second module, such as 0.3 to 3% by weight of the second module, such as 0.5 to 2% by weight of the second module.

In an advantageous embodiment of the invention the weight of the second modules is between 50 mg and 250 mg, such as between 75 mg and 150 mg.

In the present context, the invention provides an attractive bi-phasic delivery of masking, even if the delivery of nicotine is "single-phased".

In an advantageous embodiment of the invention the second module comprises nicotine in an amount of no more than 5% by weight of the module and at least 0.2 mg of nicotine by weight of the module.

In an advantageous embodiment of the invention the second module comprises at least 0.2 mg of nicotine.

In an advantageous embodiment of the invention the second module comprises between 0.2 mg and 5.0 mg of nicotine, such as between 0.5 mg and 4.0 mg of nicotine, such as between 1.0 mg and 3.0 mg of nicotine.

In an advantageous embodiment of the invention the lozenge comprises nicotine in an amount of at least 0.5 mg, such as at least 1.0 mg, such as at least 2.0 mg.

In an advantageous embodiment of the invention, the lozenge comprises nicotine in an amount of 0.5 to 8.0 mg, such as 1.0 to 6.0 mg, such as 2.0 to 4.0 mg.

In an embodiment, the nicotine of the second module is selected from the group consisting of a nicotine salt, nicotine free base, nicotine bound to an ion exchanger, such as an ion exchange resin, such as nicotine polacrilex resin, a nicotine inclusion complex or nicotine in any non-covalent binding; nicotine bound to zeolites; nicotine bound to cellulose, such as microcrystalline cellulose, or starch microspheres, and mixtures thereof.

In an advantageous embodiment of the invention the second module comprises a nicotine salt.

In an embodiment of the invention, the nicotine salt is selected from nicotine ascorbate, nicotine aspartate, nicotine benzoate, nicotine monotartrate, nicotine bitartrate, nicotine chloride (e.g., nicotine hydrochloride and nicotine dihydrochloride), nicotine citrate, nicotine fumarate, nicotine gensitate, nicotine lactate, nicotine mucate, nicotine laurate, nicotine levulinate, nicotine malate nicotine perchlorate, nicotine pyruvate, nicotine salicylate, nicotine sorbate, nicotine succinate, nicotine zinc chloride, nicotine sulfate, nicotine tosylate and nicotine salt hydrates (e.g., nicotine zinc chloride monohydrate).

In an advantageous embodiment of the invention the second module comprises nicotine bitartrate.

In an embodiment of the invention the nicotine is nicotine bitartrate.

In an advantageous embodiment of the invention the second module comprises nicotine free base.

Free base nicotine includes nicotine mixed with sugar alcohols, modified Calcium carbonate, water-soluble fibers, ion exchange resin, and combinations thereof. Nicotine bound to modified Calcium carbonate is described in international patent application WO 2010/121619, hereby incorporated by reference.

In an advantageous embodiment of the invention the first module comprises nicotine.

In an embodiment, the nicotine of the first module is selected from the group consisting of a nicotine salt, nicotine free base, nicotine bound to an ion exchanger, such as an ion exchange resin, such as nicotine polacrilex resin, a nicotine inclusion complex or nicotine in any non-covalent binding; nicotine bound to zeolites; nicotine bound to cellulose, such as microcrystalline cellulose, or starch microspheres, and mixtures thereof.

In an advantageous embodiment of the invention the first module comprises nicotine bound to an ion exchange resin.

In an advantageous embodiment the first module comprises nicotine polacrilex resin (NPR).

In an advantageous embodiment of the invention the nicotine in the first module has a slower uptake in the average mucosa than the nicotine in the second module.

In an advantageous embodiment of the invention the first module comprises a nicotine salt.

In an embodiment of the invention, the nicotine salt is selected from nicotine ascorbate, nicotine aspartate, nicotine benzoate, nicotine monotartrate, nicotine bitartrate, nicotine chloride (e.g., nicotine hydrochloride and nicotine dihydrochloride), nicotine citrate, nicotine fumarate, nicotine gensitate, nicotine lactate, nicotine mucate, nicotine laurate, nicotine levulinate, nicotine malate nicotine perchlorate, nicotine pyruvate, nicotine salicylate, nicotine sorbate, nicotine succinate, nicotine zinc chloride, nicotine sulfate, nicotine tosylate and nicotine salt hydrates (e.g., nicotine zinc chloride monohydrate).

In an advantageous embodiment of the invention the first module comprises nicotine bitartrate.

In an advantageous embodiment of the invention the second module comprises disintegrant.

In an advantageous embodiment of the invention the second module comprises disintegrant in the amount of between 0.5% and 25% by weight of the second module.

The disintegrant in the present context is referring to compounds other than sugar alcohols.

In an advantageous embodiment of the invention the disintegrant is selected from starch, pregelatinated starch, modified starch (including potato starch, maize starch, Starch 1500®, sodium starch glycolate and starch derivatives), cellulose, microcrystalline cellulose, alginates, ion-exchange resin, and superdisintegrants, such as crosslinked cellulose (such as sodium carboxy methyl cellulose), crosslinked polyvinyl pyrrolidone (PVP), crosslinked starch, crosslinked alginic acid, natural superdisintegrants, low-substituted hydroxypropylcellulose (L-HPC) and calcium silicate, and combinations thereof.

In an embodiment of the invention the disintegrant comprises cross-linked polyvinylpyrrolidone.

In an embodiment of the invention the disintegrant is cross-linked polyvinylpyrrolidone.

An advantage of using cross-linked polyvinylpyrrolidone, also known as crospovidone, as disintegrant, may be that it decreases the dependence of the disintegration time on the compression force while allowing rather low disintegration times. Also, by being more independent from compression force, a lower variation between second modules of different lozenges due to variations in compression force is facilitated.

In an embodiment of the invention at least 50% by weight of the cross-linked polyvinylpyrrolidone has a particle size below 50 micrometers.

This corresponds to commercial grades Kollidon® CL-F and Kollidon® CL-SF available from BASF.

In an embodiment of the invention at least 25% by weight of the cross-linked polyvinylpyrrolidone has a particle size below 15 micrometers.

This corresponds to commercial grade Kollidon® CL-SF available from BASF.

An advantage of the above embodiment of using cross-linked polyvinylpyrrolidone with a smaller particle size facilitates a shorter disintegration time, e.g. due to a larger relative surface of the disintegrant particles.

In an advantageous embodiment of the invention the disintegrant comprises starch.

In an advantageous embodiment of the invention the disintegrant comprises low-substituted hydroxypropylcellulose (L-HPC).

In an advantageous embodiment of the invention the disintegrant comprises super disintegrants, and wherein the amount of super disintegrant is between 2 and 13% by weight of the second module, such as between 5 and 12% by weight of the second module.

In an advantageous embodiment of the invention the super disintegrants includes crosslinked polymers.

In an advantageous embodiment of the invention the super disintegrants is selected from the group of croscarmellose sodium, crospovidone, and sodium starch glycolate.

In an advantageous embodiment of the invention the disintegrant comprises cross-linked polyvinylpyrrolidone.

In an advantageous embodiment of the invention at least 50% by weight of the cross-linked polyvinylpyrrolidone has a particle size below 50 micrometers.

In an advantageous embodiment of the invention at least 25% by weight of the cross-linked polyvinylpyrrolidone has a particle size below 15 micrometers.

In an advantageous embodiment of the invention the second module comprises disintegrant and sugar alcohol.

In an advantageous embodiment of the invention the second module comprises
nicotine in the amount of 0.2 mg to 5 mg,
sugar alcohol in the amount of 40 mg to 250 mg and
disintegrant in the amount of 5 mg to 50 mg.

In an advantageous embodiment of the invention the average particle size of the particles applied for the compression of the first module is larger than the average particle size of the particles applied for the compression of the second module.

In an advantageous embodiment of the invention the average particle size of the particles applied for the compression of the second module is smaller than 350 micrometer, such as 250 micrometer, such as 150 micrometer.

In an advantageous embodiment of the invention the particles applied for the compression of the second module comprises particles with a particle size of at least 500 micrometer, such as at least 750 micrometer, such as at least 100 micrometer.

In an embodiment of the invention, the particles applied for the compression of the second module comprises at least 10% by weight of particles with a particle size of at least 500 micrometer, such as at least 750 micrometer, such as at least 100 micrometer.

In an advantageous embodiment of the invention the first module comprises at least 50% by weight of the lozenge, such as at least 60% by weight of the lozenge.

In an advantageous embodiment of the invention the first module comprises 50% to 90% by weight of the lozenge, such as 50% to 90% by weight of the lozenge, such as 60% to 90% by weight of the lozenge, such as 70% to 90% by weight of the lozenge, such as 70% to 80% by weight of the lozenge, such as 80% to 90% by weight of the lozenge, such as 65% to 75% by weight of the lozenge.

In an advantageous embodiment of the invention the second module comprises at least 10% by weight of the lozenge, such as at least 20% by weight of the lozenge.

In an advantageous embodiment of the invention the second module comprises 10% to 50% by weight of the lozenge, such as 20% to 40% by weight of the lozenge, such as 10% to 30% by weight of the lozenge, such as 20% to 30% by weight of the lozenge.

In an advantageous embodiment of the invention second module has an exposed surface area comprises maximum 50% of a total exposed surface area of the lozenge, such as 40% of the total exposed surface area of the lozenge, such as 30% of the total exposed surface area of the lozenge, such as 20% of the total exposed surface area of the lozenge.

In an advantageous embodiment of the invention the lozenge has a maximum total volume of 0.7 cm3, such as 0.6 cm3, such as 0.5 cm3, such as 0.4 cm3, such as 0.3 cm3.

In an advantageous embodiment of the invention the lozenge has a maximum total weight of 1 gram, such as 0.9 gram, such as 0.75 gram, such as 0.5 gram, such as 0.4 gram, such as 0.3 gram.

An advantage of lozenges having a volume below the maximum stated volume is the possibility to use the lozenge discretely. Furthermore, it provides the option of self-titration.

In an advantageous embodiment of the invention, the lozenge has a total weight of 0.2 to 1 gram, such as 0.2 to 0.9 gram, such as 0.2 to 0.75 gram, such as 0.2 to 0.5 gram.

Lozenges having a volume below the maximum stated volume may provide the user with desired disintegration time and dissolution time.

In an advantageous embodiment of the invention the second module is fused by compression to the first module applying a minimum compression force of at least 10 kN, such as at least 15 kN, such as at least 20 kN, such as at least 25 kN, such as at least 30 kN.

In an embodiment of the invention the second module is fused by compression to the first module applying a minimum compression force of 10 to 40 kN, such as 15 to 40 kN, such as 20 to 40 kN, such as 25 to 40 kN, such as 30 to 40 kN.

In an embodiment of the invention the second module is fused by compression to the first module applying a minimum compression force of 10 to 40 kN, such as 15 to 35 kN, such as 20 to 30 kN.

When referring to pressing force, this refers to the applied force when using a circular punch with a diameter of 10.0 mm, unless otherwise stated. When using punches with other diameters or shapes, the pressing force is adjusted accordingly with respect to area of the punch to obtain the required punching pressure. Higher punching pressure results in higher pressure force, and vice versa.

In an advantageous embodiment of the invention the first module and second modules are two layers fused by compression.

The layers or modules of the lozenge may be formed in many different ways within the scope of the invention. As seen from above, the lozenge may be circular, oval or edged, e.g. square.

In an embodiment of the invention, the second module at least partly encapsulates the first module.

In an embodiment of the invention, the second module encapsulates the first module.

Obtaining a lozenge with a first module encapsulated by a second module may be obtained by applying a press coat as the second module around the first module.

In an advantageous embodiment of the invention the lozenge comprises the at least one sugar alcohol in an amount of at least 50% by weight of the lozenge, such as at least 60% by weight of the lozenge, such as at least 70% by weight of the lozenge.

In an embodiment of the invention, the lozenge comprises the at least one sugar alcohol in an amount of 50 to 97% by weight of the lozenge, such as 60 to 95% by weight of the lozenge, such as 70 to 90% by weight of the lozenge.

In an advantageous embodiment of the invention the at least one sugar alcohol of the second module comprises at least one sugar alcohol selected from the group of xylitol, maltitol, mannitol, erythritol, isomalt, sorbitol, lactitol or any combination thereof.

In an embodiment of the invention, the at least one sugar alcohol of the second module is selected from the group of xylitol, maltitol, mannitol, erythritol, isomalt, sorbitol, lactitol or any combination thereof.

In an embodiment of the invention, the at least one sugar alcohol in the second module comprises mannitol, erythritol or xylitol.

In an advantageous embodiment of the invention the at least one sugar alcohol of the second module comprises mannitol.

In an advantageous embodiment of the invention the at least one sugar alcohol of the second module comprises erythritol.

In an advantageous embodiment of the invention the at least one sugar alcohol of the second module has a water solubility when measured at 20 degrees Celsius of maximum 1000 g/L.

In an embodiment of the invention, the at least one sugar alcohol of the second module has a water solubility when measured at 20 degrees Celsius of 10 to 1000 g/L.

In an advantageous embodiment of the invention the second module comprises the at least one sugar alcohol in an amount of at least 50% by weight of the second module, such as at least 60% by weight of the second module, such as at least 70% by weight of the second module.

In an embodiment of the invention, the second module comprises the at least one sugar alcohol in an amount of 50 to 97% by weight of the second module, such as 60 to 95% by weight of the second module, such as 70 to 90% by weight of the second module.

In an advantageous embodiment of the invention the at least one sugar alcohol of the second module comprises non-DC (non-direct compressible) grade sugar alcohol.

In an advantageous embodiment of the invention the at least one sugar alcohol of the first module comprises at least one sugar alcohol selected from the group of xylitol, maltitol, mannitol, erythritol, isomalt, sorbitol, lactitol or any combination thereof.

In an embodiment of the invention, the at least one sugar alcohol of the first module is selected from the group of xylitol, maltitol, mannitol, erythritol, isomalt, sorbitol, lactitol or any combination thereof.

In an advantageous embodiment of the invention the at least one sugar alcohol of the first module is selected from the group of mannitol, erythritol, isomalt, sorbitol, or any combination thereof.

In an advantageous embodiment of the invention the first module comprises the at least one sugar alcohol in an amount of at least 50% by weight of the first module, such as at least 60% by weight of the second module, such as at least 70% by weight of the first module.

In an embodiment of the invention, the first module comprises the at least one sugar alcohol in an amount of 50 to 97% by weight of the first module, such as 60 to 95% by weight of the first module, such as 70 to 90% by weight of the first module.

In an advantageous embodiment of the invention the lozenge is substantially free of mono- and disaccharides.

In an advantageous embodiment of the invention the lozenge comprises a pH regulating agent.

In an advantageous embodiment of the invention the pH regulating agent is selected from carbonates, including monocarbonate, bicarbonate and sesquicarbonate, glycerinate, phosphate, glycerophosphate, acetate, glyconate or citrate of an alkali metal, ammonium, tris buffer, amino acids, and any combination thereof.

In an embodiment of the invention, encapsulated buffer such as Effer-Soda® may also be used.

In an advantageous embodiment of the invention the pH regulating agent is selected from sodium carbonate, sodium bicarbonate, potassium phosphate, potassium carbonate, potassium bicarbonate, and any combination thereof.

Combinations of a carbonate and a bicarbonate may be especially advantageous. Such combination may e.g. be a sodium carbonate-sodium bicarbonate buffer system, e.g. sodium carbonate and sodium bicarbonate in a weight-ratio between 5:1 and 2.5:1, preferably in a weight-ratio between 4.1:1 and 3.5:1.

In an advantageous embodiment of the invention the pH regulating agent comprises or is sodium carbonate.

In an advantageous embodiment of the invention the lozenge comprises pH regulating agent in an amount of at least 0.2% by weight of the lozenge, such as at least 0.3% by weight of the lozenge, such as at least 0.4% by weight of the lozenge, such as at least 0.5% by weight of the lozenge.

In an embodiment of the invention, the lozenge comprises pH regulating agent in an amount of 0.2 to 7% by weight of the lozenge, such as 0.2 to 6% by weight of the lozenge, such as 0.2 to 5% by weight of the lozenge, such as 0.3 to 4% by weight of the lozenge, such as 0.4 to 3% by weight of the lozenge, such as 0.5 to 2% by weight of the lozenge.

In an advantageous embodiment of the invention the lozenge is free of pH regulating agent.

In an advantageous embodiment of the invention the first module comprises pH regulating agent.

In an advantageous embodiment of the invention the first module comprises pH regulating agent in an amount of at least 0.2% by weight of the first module, such as at least 0.3% by weight of the first module, such as at least 0.4% by weight of the first module, such as at least 0.5% by weight of the first module.

In an embodiment of the invention, the first module comprises pH regulating agent in an amount of 0.2 to 7% by weight of the first module, such as 0.2 to 6% by weight of the first module, such as 0.2 to 5% by weight of the first module, such as 0.3 to 4% by weight of the first module, such as 0.4 to 3% by weight of the first module, such as 0.5 to 2% by weight of the first module.

In an embodiment of the invention, the first module is free of pH regulating agent.

In an advantageous embodiment of the invention the second module comprises pH regulating agent.

In an advantageous embodiment of the invention the second module comprises pH regulating agent in an amount of at least 0.2% by weight of the second module, such as at least 0.3% by weight of the second module, such as at least 0.4% by weight of the second module, such as at least 0.5% by weight of the second module.

In an embodiment of the invention, the second module comprises pH regulating agent in an amount of 0.2 to 7% by weight of the second module, such as 0.2 to 6% by weight of the second module, such as 0.2 to 5% by weight of the second module, such as 0.3 to 4% by weight of the second module, such as 0.4 to 3% by weight of the second module, such as 0.5 to 2% by weight of the second module.

The pH regulating agents, such as alkaline buffering agents, suitable for use in the present invention include, but are not limited to, sodium carbonate, sodium bicarbonate, potassium phosphate, potassium carbonate and potassium bicarbonate. In one embodiment, the buffering agents are selected from potassium bicarbonate, sodium carbonate and mixtures thereof. The pH regulating agents, e.g. buffering agents, may be incorporated in the first and/or the second module. The total amount of buffer present in the compositions of the present invention is from about 5 mg to about 20 mg. In one embodiment the total amount of buffer present in the compositions of the present invention is from about 8 mg to about 12 mg. In one embodiment the ratio of nicotine to total buffer is from about 3:1 to about 1:3 by total weight.

In an embodiment of the invention, the second module comprises pH regulating agent in an amount of 2.0 to 8.0% by weight of the second module, such as 2.7 to 5.7% by weight of the second module.

In an advantageous embodiment of the invention the pH regulating agent is a basic pH regulating agent.

Thus, in the above embodiment the pH regulating agent of the first and/or second module is a basic pH regulating agent.

In an advantageous embodiment of the invention the pH regulating agent is a buffering agent.

Thus, in the above embodiment the pH regulating agent of the first and/or second module is a buffering agent.

In an advantageous embodiment of the invention the pH regulating agent is a basic buffering agent.

Thus, in the above embodiment the pH regulating agent of the first and/or second module is a basic buffering agent.

In an advantageous embodiment of the invention the formulation provides a peak saliva concentration of nicotine of more than 0.3 mg/mL, such as more than 0.5 mg/mL.

In an advantageous embodiment of the invention the formulation provides a peak saliva pH of more than 8 during the first 120 seconds upon oral administration.

In an advantageous embodiment of the invention the lozenge comprises high intensity sweetener.

In an embodiment of the invention, the high intensity sweetener is selected from sucralose, aspartame, salts of acesulfame, such as acesulfame potassium, alitame, saccharin and its salts, cyclamic acid and its salts, glycyrrhizin, dihydrochalcones, thaumatin, monellin, stevioside, and any combination thereof.

In an embodiment of the invention, the high intensity sweetener is comprised in the first module.

In an embodiment of the invention, the high intensity sweetener is comprised in the second module.

In an embodiment of the invention, the high intensity sweetener is comprised in the first and second module.

In an advantageous embodiment of the invention the lozenge comprises flavor.

In an advantageous embodiment of the invention the lozenge comprises flavor in an amount of at least 0.1% by weight of the lozenge.

In an embodiment of the invention, the lozenge comprises flavor in an amount of 0.1 to 15.0% by weight of the lozenge, such as 0.1 to 10.0% by weight of the lozenge, such as 0.1 to 5.0% by weight of the lozenge, such as 0.2 to 3.0% by weight of the lozenge.

In an embodiment of the invention the first module comprises flavor.

In an embodiment of the invention the first module comprises flavor in an amount of at least 0.1% by weight of the first module.

In an embodiment of the invention, the first module comprises flavor in an amount of 0.1 to 15.0% by weight of the first module, such as 0.1 to 10.0% by weight of the first module, such as 0.1 to 5.0% by weight of the first module, such as 0.2 to 3.0% by weight of the first module.

In an embodiment of the invention the second module comprises flavor.

In an embodiment of the invention the second module comprises flavor in an amount of at least 0.1% by weight of the second module.

In an embodiment of the invention, the second module comprises flavor in an amount of 0.1 to 15.0% by weight of the second module, such as 0.1 to 10.0% by weight of the second module, such as 0.1 to 5.0% by weight of the second module, such as 0.2 to 3.0% by weight of the second module.

In an advantageous embodiment of the invention the flavor is selected from the group of menthol, peppermint, wintergreen, sweet mint, spearmint, vanillin, chocolate, coffee, cinnamon, clove, tobacco, citrus and fruit flavors and mixtures thereof.

Flavors may e.g. be present in an amount about 1 mg to about 100 mg per lozenge.

In an advantageous embodiment of the invention the first module comprises at least one mucoadhesive in the amount of 0.5 to 10% by weight of the first module.

In an advantageous embodiment of the invention the first module comprises dissolution modifiers.

In an advantageous embodiment of the invention the dissolution modifiers comprise any of, but are not limited to, acacia, agar, alginic acid or a salt thereof, carbomer, carboxymethylcellulose, carrageenan, cellulose, chitosan, copovidone, cyclodextrins, ethylcellulose, gelatin, guar gum, hydroxyethyl cellulose, hydroxyethyl methylcellulose, hydroxypropyl cellulose, hypromellose, inulin, methylcellulose, pectin, polycarbophil or a salt thereof, polyethylene glycol, polyethylene oxide, polyvinyl alcohol, pullulan, starch, tragacanth, trehalose, xanthan gum and mixtures thereof.

In one embodiment, the dissolution modifiers included within the formulations of the present invention may be selected from the group consisting of alginic acid or a salt thereof, polycarbophil or a salt thereof, xanthan gum and mixtures thereof. In one embodiment, dissolution modifier is used in an amount of from about 10 mg to about 30 mg per lozenge, in another embodiment from about 15 mg to about 25 mg per lozenge.

In an advantageous embodiment of the invention the second module comprises binder, such as microcrystalline cellulose, hydroxypropyl cellulose (HPC), or a mixture thereof.

In an advantageous embodiment of the invention the first module comprises binder, such as microcrystalline cellulose, hydroxypropyl cellulose (HPC), or a mixture thereof.

In an advantageous embodiment of the invention the lozenge has a breaking point of at least 100 N, such as at least 150 N, such as at least 200 N.

In an embodiment of the invention, the lozenge has a breaking point of 100 N to 400N, such as 150 N to 400N, such as 200 N to 400N.

In an embodiment of the invention, the breaking point is measured by a PTB 311 from Pharma Test.

The invention further relates to a method of manufacturing a water-dissolvable compressed oral nicotine lozenge, the method comprising the steps of providing a first powdered composition and a second powdered composition, the first powdered composition comprising at least one sugar alcohol, the second powdered composition comprising at least one sugar alcohol and nicotine, pressing the first powdered composition and the second powdered composition to obtain a lozenge module fused by compression to an FDT-module.

In an advantageous embodiment of the invention the method comprises
pressing the first powdered composition to obtain a lozenge module, and
pressing the lozenge module and the second powdered composition to obtain an FDT-module fused by compression to the lozenge module.

In an advantageous embodiment of the invention the method comprises
pressing the second powdered composition to obtain an FDT-module, and
pressing the FDT-module and the first powdered composition to obtain a lozenge module fused by compression to the FDT-module.

In an advantageous embodiment the pressing is performed with a pressing force of at least 5 kN, such as at least 10 kN, such as at least 15 kN, such as at least 20 kN.

When referring to pressing force, this refers to the applied force when using a circular punch with a diameter of 10.0 mm, unless otherwise stated. When using punches with other diameters or shapes, the pressing force is adjusted accordingly with respect to area of the punch to obtain the required punching pressure. Higher punching pressure results in higher pressure force, and vice versa.

In an embodiment of the invention, the pressing is performed with a pressing force of 5 to 40 kN, such as 10 to 40 kN, such as 15 to 40 kN, such as 20 to 40 kN.

In an embodiment of the invention, the water-dissolvable compressed oral nicotine lozenge of the invention or any of its embodiments is obtained by the method of the invention or any of its embodiments.

The invention further relates to a water-dissolvable compressed oral nicotine lozenge comprising a first module and a second module,
the first and the second modules being fused by compression,
the first module being a lozenge module and
the second module being an FDT-module comprising nicotine.

In an embodiment of the invention, the water-dissolvable compressed oral nicotine lozenge according to the embodiment is made in accordance with the water-dissolvable compressed oral nicotine lozenge first described or any of its embodiments, or obtained by the method of the invention or any of its embodiments.

DETAILED DESCRIPTION

As used herein the term "water-dissolvable compressed oral nicotine lozenge" refers to a compressed tablet that overall is slowly dissolvable in water. While the nicotine lozenge of the invention comprises a fast dissolvable FDT module, it also comprises a slowly dissolvable lozenge module. The nicotine lozenge of course does not comprise e.g. chewing gum modules that does not dissolve in water. Furthermore, the nicotine lozenge is water-dissolvable in the sense that it disintegrates and that main constituents dissolve in water. The nicotine lozenge of the invention is a compressed lozenge, formed by compression of at least a first powdered composition and a second powdered composition to give the first and second layer, respectively. The nicotine lozenge may comprise some amounts of water-insoluble material, such as e.g. MCC. For example, the nicotine lozenge may dissolve within a period of at least 2 minutes upon oral administration, such as at least 3 minutes, such as at least 4 minutes, such as at least 5 minutes.

As used herein, the term "FDT-module" (Fast Disintegrating Tablet-module) refers to a module of a lozenge for oral administration. The FDT module disintegrates in the oral cavity relatively fast from the administration, such as within about 60 seconds from oral administration.

As used herein the term "lozenge module" refers to a module imparting lozenge properties, i.e. a module that dissolve or disintegrate slowly in the mouth, whereby its constituents are slowly released, e.g. pH regulating agents, flavor, nicotine etc. depending on the specific embodiment. For example, the lozenge module may dissolve within a period of at least 2 minutes upon oral administration, such as at least 3 minutes, such as at least 4 minutes, such as at least 5 minutes.

As used herein, the term "disintegrate" refers to a reduction of an object to components, fragments or particles. Disintegration time may be measured in vitro or in vivo. Unless otherwise stated, the in vitro measurements are carried out in accordance to European Pharmacopeia 9.0, section 2.9.1, Disintegration of tablets and capsules.

As used herein, the term "dissolve" is the process where a solid substance enters a solvent (oral saliva) to yield a solution. Unless otherwise stated, dissolving implies a full dissolving of the compound in question.

As used herein, the term "disintegrant" refers to an ingredient facilitating disintegration of an FDT-module, when the FDT-module comes into contact with saliva. Disintegrants usable within the scope of the invention may include starch, pregelatinated starch, modified starch (including potato starch, maize starch, Starch 1500®, sodium starch glycolate and starch derivatives), cellulose, microcrystalline cellulose, alginates, ion-exchange resin, and superdisintegrants, such as crosslinked cellulose (such as sodium carboxy methyl cellulose), crosslinked polyvinyl pyrrolidone (PVP), crosslinked starch, crosslinked alginic acid, natural superdisintegrants, and calcium silicate. Disintegrants may often be considered as measure promoting the break-up of the module into smaller fragments upon administration to facilitate nicotine release and eventual absorption.

As used herein, the term "nicotine" refers to nicotine in any form, including free base nicotine, nicotine salts, nicotine bound to ion exchange resins, such as nicotine polacrilex, nicotine bound to zeolites; nicotine bound to cellulose, such as fibers of microcrystalline cellulose, such as of microbial origin, or starch microspheres, nicotine bound to $CaCO_3$, and mixtures thereof. Thus, when referring to nicotine amounts also to be understood as the nicotine dose, the amounts refers to the amount of pure nicotine. Thus, when measuring the concentration of nicotine added as nicotine salt, it is the mass of the equivalent amount of pure nicotine, not the mass of the salt, that is relevant. Nicotine also covers nicotine not obtained from tobacco, often referred to as synthetic nicotine. Nicotine is included in the second layer, and in some embodiments also in the first layer. In other embodiments nicotine is included in the second layer but not in the first layer.

As used herein, the term "nicotine salt" refers to nicotine in ionized form bound to a counterion.

As used herein, the term "NBT" refers to nicotine bitartrate and hydrates thereof.

As used herein, the term "%" and "percent" refers to percent by weight, unless otherwise is stated.

As used herein, the term "release of nicotine" refers to the nicotine being made bioavailable, i.e. available for absorption over the mucous membrane in the oral cavity. While some forms of nicotine require dissolution for being bioavailable, other forms may be readily absorbed into the body without dissolution. For example, in order for the nicotine to be bioavailable, the matrix of the solid formulation should be disintegrated. Some forms of nicotine require the nicotine to further be released from e.g. a carrier, e.g. nicotine from a nicotine-ion exchange resin such as nicotine polacrilex. Other nicotine forms, such nicotine salts, hereunder nicotine bitartrate, may readily dissolve upon disintegration of the matrix of the solid formulation. Still, some nicotine forms may not require dissolving. This applies for e.g. nicotine free base, which is released upon disintegration of the solid formulation matrix.

As used herein, the term "pH regulating agent" refers to agents, which active adjust and regulates the pH value of the solution to which they have been added or are to be added. Thus, pH regulating agents may be acids and bases, including acidic buffering agents and alkaline buffering agents. On the other hand, pH regulating agents does not including substances and compositions that can only affect the pH by dilution. Furthermore, pH regulating agents does not include e.g. flavoring, fillers, etc.

As used herein, the term "buffering agent" is used interchangeably with "buffer" and refers to agents for obtaining a buffer solution. Buffering agents include acidic buffering agents, i.e. for obtaining a buffer solution with an acidic pH, and alkaline buffering agents, i.e. for obtaining a buffer solution with an alkaline pH.

In embodiments where the lozenge comprises fillers, different fillers may be used. Microcrystalline cellulose may be used as a filler in some embodiments of the invention. Examples of usable fillers include magnesium- and calcium carbonate, sodium sulphate, ground limestone, silicate compounds such as magnesium- and aluminum silicate, kaolin and clay, aluminum oxide, silicium oxide, talc, titanium oxide, mono-, di- and tri-calcium phosphates, cellulose polymers, such as wood, starch polymers, fibers and combinations thereof.

In embodiments of the invention mannitol is used as a bulk sweetener. Other usable sweeteners include sugar sweetener and/or sugarless sweetener.

The sweeteners may often support the flavor profile of the formulation.

Sugar sweeteners generally include, but are not limited to saccharide-containing components, such as sucrose, dextrose, maltose, saccharose, lactose, sorbose, dextrin, trehalose, D-tagatose, dried invert sugar, fructose, levulose, galactose, corn syrup solids, glucose syrup, hydrogenated glucose syrup, and the like, alone or in combination. These sugar sweeteners may also be included as a humectant.

Sugarless sweeteners generally include, but are not limited to sugar alcohols (also sometimes referred to as polyols) such as sorbitol, erythritol, xylitol, maltitol, mannitol, lactitol, and isomalt.

Examples of usable disintegrants include starch, pregelatinated starch, modified starch (including potato starch, maize starch, Starch 1500®, sodium starch glycolate and starch derivatives), cellulose, microcrystalline cellulose, alginates, ion-exchange resin, and superdisintegrants, such as crospovidone, croscarmellose sodium, and sodium starch glycolate, crosslinked cellulose (such as sodium carboxy methyl cellulose), crosslinked polyvinyl pyrrolidone (PVP), crosslinked starch, crosslinked alginic acid, natural superdisintegrants, and calcium silicate, and combinations thereof.

Usable high intensity sweeteners include, but are not limited to sucralose, aspartame, salts of acesulfame, such as acesulfame potassium, alitame, saccharin and its salts, cyclamic acid and its salts, glycyrrhizin, dihydrochalcones, thaumatin, monellin, stevioside and the like, alone or in combination.

Usable flavors include almond, almond amaretto, apple, Bavarian cream, black cherry, black sesame seed, blueberry, brown sugar, bubblegum, butterscotch, cappuccino, caramel, caramel cappuccino, cheesecake (graham crust), cinnamon redhots, cotton candy, circus cotton candy, clove, coconut, coffee, clear coffee, double chocolate, energy cow, graham cracker, grape juice, green apple, Hawaiian punch, honey, Jamaican rum, Kentucky bourbon, kiwi, koolada, lemon, lemon lime, tobacco, maple syrup, maraschino cherry, marshmallow, menthol, milk chocolate, mocha, Mountain Dew, peanut butter, pecan, peppermint, raspberry, banana, ripe banana, root beer, RY 4, spearmint, strawberry, sweet cream, sweet tarts, sweetener, toasted almond, tobacco, tobacco blend, vanilla bean ice cream, vanilla cupcake, vanilla swirl, vanillin, waffle, Belgian waffle, watermelon, whipped cream, white chocolate, wintergreen, amaretto, banana cream, black walnut, blackberry, butter, butter rum, cherry, chocolate hazelnut, cinnamon roll, cola, creme de menthe, eggnog, English toffee, guava, lemonade, licorice, maple, mint chocolate chip, orange cream, peach, pina colada, pineapple, plum, pomegranate, pralines and cream, red licorice, salt water taffy, strawberry banana, strawberry kiwi, tropical punch, tutti frutti, vanilla, or any combination thereof.

According to an embodiment of the invention, flavor may be used as taste masking for the nicotine.

In some embodiments of the invention, the first and/or second module comprises pH regulating agent.

In some embodiments of the invention, the pH regulating agent comprises buffer.

Usable buffering agents include carbonate, including monocarbonate, bicarbonate and sesquicarbonate, glycerinate, phosphate, glycerophosphate, acetate, glyconate or citrate of an alkali metal, ammonium, tris buffer, amino acids and mixtures thereof. Encapsulated buffer such as EfferSoda® may also be used.

The buffering agent may be added to the formulation of the first and/or second module together with the water-soluble ingredients. Buffering agent in the lozenge may be used to obtain the desired pH-values in the saliva of a lozenge user.

In some embodiments, the buffering agent comprises sodium carbonate and sodium bicarbonate, e.g. in a weight-ratio between 5:1 and 2.5:1, preferably in a weight-ratio between 4.1:1 and 3.5:1.

Silicon dioxide may be used as a glidant. Other glidants usable for the formulation may also be used within the scope of the invention.

Magnesium stearate and/or sodium stearyl fumerate may be used as a lubricant. Other lubricants usable for the formulation may also be used within the scope of the invention.

Ready to use systems may be used within the scope of the invention. Typically, such ready-to-use systems may e.g. replace filler, disintegrant, glidant or similar with a single powder mix. Suitable ready-to-use systems for the purpose, but not limited to, include Pearlitol® Flash (Roquette), Pharmaburst® 500 (SPI Pharma), Ludiflash® (BASF), ProSolv® (JRS Pharma), ProSolv® EasyTab (JRS Pharma), F-Melt® (Fuji Chemical), SmartEx® 50/100 (Shin Etsu/Harke Pharma). Using a ready to use systems comprising a disintegrant may be especially advantageous.

In order to obtain an FDT-module being designed for disintegrating within a period of 60 second upon oral administration, a range of parameters can be adjusted.

First, by varying the composition, the disintegration time can be altered. Using ingredients with a high water-solubility may facilitate a lowered disintegration time.

Particularly, including a disintegrant may significantly influence the disintegration time, subject to the total composition of the second module. Also, by varying the amount and type of the disintegrant, the disintegration time may be further adjusted. For example, if the second layer having a lower disintegration time is desired, the percentage content of disintegrant may be increased and/or the type of disintegrant may be at least partly exchanged for a more effective disintegrant.

Also, decreasing the particle size of the disintegrant tends to lower the disintegration time, likely due to an increased surface area to volume ratio.

Furthermore, the compression force used to press the second module correlate significantly with the obtained hardness of the second module, such that a high compression force typically increases the hardness of the obtained second module. By adjusting the hardness of a second module, the disintegration time may also be influenced, such that a lowered hardness typically gives a shorter disintegration time. Here it has been observed for a number of compositions that by applying the correct compression force a disintegration time below 60 seconds upon oral administration can be achieved, whereas a too high compression force may result in a longer disintegration time above 60 seconds. In this regard it is noted that the threshold compression force may vary significantly, depending on other parameters, such as overall composition, content and type of disintegrant, etc. When, for example, a certain setup results in a too slow disintegration, a further way of adjusting may be to replace a regular disintegrant with a superdisintegrant, i.e. which facilitates disintegration in a more efficient way.

Increasing the water-solubility may also be facilitated by exchanging ingredients with low water-solubility with ingredients having higher water-solubility. For example, using sugar alcohols as fillers may be very advantageous insofar that the sugar alcohols have a higher water solubility than alternative fillers.

Moreover, using sugar alcohols with a lower compactibility leads to lower disintegration time. Too low compactibility may compromise the mechanical strength of the second module and the lozenge and lead to undesirably high friability and risk of cracks etc.

Further examples of parameters that may be adjusted in order to obtain a second module being designed for disintegrating within a period of 60 second upon oral administration include size and shape of the second module and the lozenge. The larger volume of the second module, the longer the disintegration time and thus release time of the nicotine and pH regulating agent.

For example, increasing the flatness (e.g. quantified by a diameter to height ratio) for e.g. a disc-shaped lozenges typically decreases disintegration time by increasing the surface-to-volume. As long as the lozenge has a satisfactory mechanical strength, flatness may be increased.

Also, modifying the cross-sectional profile from a convex type lozenge to a concave shaped lozenge lowers the disintegration time. It is noted that this may to some degree lower the mechanical strength of the lozenge, however, as long as it is satisfactory, pursuing the concave cross-section may help to increase disintegration and thus lower the disintegration time.

Also, when using binders, e.g. to obtain a higher cohesiveness and mechanical strength of the lozenge, the amount of such binders may be decreased as much as possible to obtain a higher disintegration rate and thus a shorter disintegration time. Some disintegrants may also function as binders, e.g. PVP.

Furthermore, by adding a salivation agent to the nicotine lozenge, an increased amount of saliva in the vicinity of the lozenge may be facilitated, which again supports the dissolving and disintegration of the second module to reduce the disintegration time.

Further, the type and amount of lubricant, if any, may be adjusted to optimize disintegration time. For example, using Sodium stearyl fumarate (SSF) typically leads to a lower disintegration time compared to when using magnesium stearate MgSt.

Thus, a wide range of parameters may be adjusted when designing the second module with a disintegration time of 60 second upon oral administration.

Typically, the formulation of the second module may comprise ingredients selected from the group consisting of bulk sweeteners, fillers, ready to use systems, flavors, drybinders, disintegrant, hereunder superdisintegrants, tabletting aids, anti-caking agents, emulsifiers, antioxidants, enhancers, absorption enhancers, buffering agents, high intensity sweeteners, colors, glidants, lubricants, or any combination thereof. Absorption enhancers may include e.g. pH regulating agents, such as buffering agents, and mucoadhesive.

According to an embodiment of the invention, at least a part of the nicotine is adhered to dry-binder particles.

According to an embodiment of the invention, an amount of dry-binder is used to adhere nicotine to bulk sweetener.

EXAMPLES

Examples 1-8

Variation of Nicotine Amount 500 mg nicotine lozenges were made each with 350 mg first module and 150 mg second module.

The composition of layer 1 is prepared by pouring about half of the sugar alcohol into a mixing bowl, followed by the remaining ingredients except lubricant, and finally the remaining sugar alcohol. The ingredients are tumbled/mixed with a mixer (Turbula® or Duma) for 4-10 min at 49 rpm.

A premade MgSt-Sugar alcohol mixture, made by mixing MgSt with about 5% of the sugar alcohol in a mixer (Turbula® or Duma) for 1 min at 49 rpm, is added and the ingredients are further mixed for 1-2 min at 49 rpm.

The composition of layer 2 is prepared by pouring all the ingredients except lubricant, into a mixing bowl. The ingredients are tumbled/mixed with a mixer (Turbula® or Duma) for 4-10 min at 49 rpm.

A premade MgSt-Sugar alcohol mixture, made by mixing MgSt with about 5% of the sugar alcohol in a mixer (Turbula® or Duma) for 1 min at 49 rpm, is added and the ingredients are further mixed for 1-2 min at 49 rpm.

The lubricated powder blends are sequentially transferred to the hopper of a tableting machine.

Layer 1 is then compressed at a compression force of about 3 kN, after which layer 2 is fused by compression to layer 1 at a compression force of about 15-20 kN. Punch used: 10.00 mm, circular, shallow concave, D tooling.

The fast disintegrating tablets are manufactured on a lab scale machine, for example RIVA Piccola bi-layer tablet press. The tablet machine is commissioned by adjusting the fill depth and compression force so the weight and hardness of lozenges match the acceptance criteria. A pre-compression force could be included to avoid capping.

TABLE 1

Compositions of first and second layers.

| | Ex | | | | | | | |
|---|---|---|---|---|---|---|---|---|
| | 1 | 2 | 3 | 4 | 5 | 6 | 7 | 8 |
| Raw material layer 1 | Content in weight percent of Layer 1 | | | | | | | |
| Mannitol | 97.75 | 97.75 | 97.75 | 97.75 | 97.75 | 97.75 | 97.75 | 97.75 |
| Buffer | 0.5 | 0.5 | 0.5 | 0.5 | 0.5 | 0.5 | 0.5 | 0.5 |
| Flavor | 1 | 1 | 1 | 1 | 1 | 1 | 1 | 1 |
| HIS | 0.25 | 0.25 | 0.25 | 0.25 | 0.25 | 0.25 | 0.25 | 0.25 |
| MgSt | 0.5 | 0.5 | 0.5 | 0.5 | 0.5 | 0.5 | 0.5 | 0.5 |
| Total layer 1 | 100 | 100 | 100 | 100 | 100 | 100 | 100 | 100 |
| Raw material layer 2 | Content in weight percent of Layer 2 | | | | | | | |
| Mannitol | 88.75 | 87.25 | 85.75 | 84.25 | 82.75 | 81.25 | 78.25 | 75.25 |
| Disintegrant | 8 | 8 | 8 | 8 | 8 | 8 | 8 | 8 |
| Flavor | 1 | 1 | 1 | 1 | 1 | 1 | 1 | 1 |
| HIS | 0.25 | 0.25 | 0.25 | 0.25 | 0.25 | 0.25 | 0.25 | 0.25 |
| NBT | 1.5 | 3.0 | 4.5 | 6.0 | 7.5 | 9 | 12.0 | 15.0 |
| MgSt | 0.5 | 0.5 | 0.5 | 0.5 | 0.5 | 0.5 | 0.5 | 0.5 |
| Total layer 2 | 100 | 100 | 100 | 100 | 100 | 100 | 100 | 100 |

NBT = Nicotine bi-tartrate (nicotine content of 32.38% by weight)

Mannitol may be used as the sugar alcohol in layer 1 and layer 2. Other usable sugar alcohols for use in layer 1 may include sorbitol, erythritol, xylitol, maltitol, lactitol, and isomalt. Of these isomalt, erythritol, and sorbitol are particularly preferred. Other usable sugar alcohols for use in layer 2 may include sorbitol, erythritol, xylitol, maltitol, lactitol, and isomalt. The disintegrant in layer 2 may e.g. be a starch based disintegrant. In embodiments of the invention, the disintegrant may be supplied as part of a ready to use system, e.g. Pearlitol® Flash from Roquette, a mannitol-based product comprising approximately 17% by weight of disintegrant. Examples of other usable ready to use system include e.g. Pharmaburst® 500 (SPI Pharma), Ludiflash® (BASF), ProSolv® (JRS Pharma), ProSolv® EasyTab (JRS Pharma), F-Melt® (Fuji Chemical), SmartEx® 50/100 (Shin Etsu/Harke Pharma).

Preferred high intensity sweeteners (HIS) may e.g. be sucralose, acesulfame potassium, and mixtures thereof. Other high intensity sweeteners, such as aspartame, salts of acesulfame, such as acesulfame potassium, alitame, saccharin and its salts, cyclamic acid and its salts, glycyrrhizin, dihydrochalcones, thaumatin, monellin, stevioside, alone or in combination, are also usable within the scope of the invention.

Menthol, peppermint, and mixtures thereof may be used in the above formulations as flavors. Other flavors may also be used within the scope of the invention.

Sodium carbonate may be used as the buffer. Further usable buffers include other carbonates, including monocarbonates, bicarbonates and sesquicarbonates, glycerinate, phosphate, glycerophosphate, acetate, glyconate or citrate of an alkali metal, ammonium, tris buffer, amino acids and mixtures thereof.

In the above MgSt (Magnesium stearate) is used as lubricant. Other lubricants, such as sodium stearyl fumerate may also be usable within the scope of the invention.

In examples 1-8, starch is used as a disintegrant. Examples of other usable disintegrates include e.g. pregelatinated starch, modified starch (including potato starch, maize starch, Starch 1500®, sodium starch glycolate and starch derivatives), cellulose, microcrystalline cellulose, alginates, and ion-exchange resin.

Examples 9-16

Use of Superdisintegrant 500 mg nicotine lozenges where made each with 350 mg first module and 150 mg second module.

The lozenges were prepared as described for example 1-8.

TABLE 2

Compositions of first and second layers.

| | Ex | | | | | | | |
|---|---|---|---|---|---|---|---|---|
| | 9 | 10 | 11 | 12 | 13 | 14 | 15 | 16 |
| Raw material | Content in weight percent of Layer 1 | | | | | | | |
| Mannitol | 97.75 | 97.75 | 97.75 | 97.75 | 97.75 | 97.75 | 97.75 | 97.75 |
| Buffer | 0.5 | 0.5 | 0.5 | 0.5 | 0.5 | 0.5 | 0.5 | 0.5 |
| Flavor | 1.0 | 1.0 | 1.0 | 1.0 | 1.0 | 1.0 | 1.0 | 1.0 |

TABLE 2-continued

Compositions of first and second layers.

| | \multicolumn{8}{c}{Ex} | | | | | | | |
|---|---|---|---|---|---|---|---|---|
| | 9 | 10 | 11 | 12 | 13 | 14 | 15 | 16 |
| HIS | 0.25 | 0.25 | 0.25 | 0.25 | 0.25 | 0.25 | 0.25 | 0.25 |
| MgSt | 0.5 | 0.5 | 0.5 | 0.5 | 0.5 | 0.5 | 0.5 | 0.5 |
| Total layer 1 | 100 | 100 | 100 | 100 | 100 | 100 | 100 | 100 |
| Raw material | \multicolumn{8}{c}{Content in weight percent of Layer 2} | | | | | | | |
| Mannitol | 94.25 | 93.25 | 91.25 | 89.25 | 87.25 | 85.25 | 83.25 | 81.25 |
| Superdisintegrant | 1 | 2 | 4 | 6 | 8 | 10 | 12 | 14 |
| Flavor | 1.0 | 1.0 | 1.0 | 1.0 | 1.0 | 1.0 | 1.0 | 1.0 |
| HIS | 0.25 | 0.25 | 0.25 | 0.25 | 0.25 | 0.25 | 0.25 | 0.25 |
| NBT | 3.0 | 3.0 | 3.0 | 3.0 | 3.0 | 3.0 | 3.0 | 3.0 |
| MgSt | 0.5 | 0.5 | 0.5 | 0.5 | 0.5 | 0.5 | 0.5 | 0.5 |
| Total layer 2 | 100 | 100 | 100 | 100 | 100 | 100 | 100 | 100 |

NBT = Nicotine bi-tartrate (nicotine content of 32.38% by weight)

In Ex 9-16 Crospovidone is used as a superdisintegrant. Alternative superdisintegrants may e.g. include crosslinked cellulose (such as sodium carboxy methyl cellulose), cross-linked starch, crosslinked alginic acid, natural superdisintegrants, low-substituted hydroxypropylcellulose (L-HPC) and calcium silicate.

Alternative ingredients as described in relation to examples 1-8 may also be applied for examples 9-16.

Examples 17-24

Use of Disintegrant 500 mg nicotine lozenges where made each with 350 mg first module and 150 mg second module.

The lozenges were prepared as described for example 1-8.

The indicated content of starch disintegrant is included as part of the Pearlitol® Flash, a commercially available ready to use system from Roquette.

Pearlitol® Flash is used comprising approximately 17% by weight of starch disintegrant. Examples of other usable ready to use system include e.g. Pharmaburst® 500 (SPI Pharma), Ludiflash® (BASF), ProSolv® (JRS Pharma), ProSolv® EasyTab (JRS Pharma), F-Melt® (Fuji Chemical), SmartEx® 50/100 (Shin Etsu/Harke Pharma).

Alternative ingredients as described in relation to examples 1-16 may also be applied for examples 17-24.

Examples 25-32

500 mg nicotine lozenges where made each with 350 mg first module and 150 mg second module.

TABLE 3

Compositions of first and second layers.

| | \multicolumn{8}{c}{Ex} | | | | | | | |
|---|---|---|---|---|---|---|---|---|
| | 17 | 18 | 19 | 20 | 21 | 22 | 23 | 24 |
| Raw material | \multicolumn{8}{c}{Content in weight percent of Layer 1} | | | | | | | |
| Mannitol | 97.75 | 97.75 | 97.75 | 97.75 | 97.75 | 97.75 | 97.75 | 97.75 |
| Buffer | 0.5 | 0.5 | 0.5 | 0.5 | 0.5 | 0.5 | 0.5 | 0.5 |
| Flavor | 1.0 | 1.0 | 1.0 | 1.0 | 1.0 | 1.0 | 1.0 | 1.0 |
| HIS | 0.25 | 0.25 | 0.25 | 0.25 | 0.25 | 0.25 | 0.25 | 0.25 |
| MgSt | 0.5 | 0.5 | 0.5 | 0.5 | 0.5 | 0.5 | 0.5 | 0.5 |
| Total layer 1 | 100 | 100 | 100 | 100 | 100 | 100 | 100 | 100 |
| Raw material | \multicolumn{8}{c}{Content in weight percent of Layer 2 Content of starch disintegrant} | | | | | | | |
| | 2 | 4 | 6 | 8 | 10 | 12 | 14 | 16 |
| Mannitol | 84.95 | 73.25 | 61.45 | 49.65 | 37.95 | 26.15 | 14.35 | 2.65 |
| Pearlitol Flash | 11.8 | 23.5 | 35.3 | 47.1 | 58.8 | 70.6 | 82.4 | 94.1 |
| Flavor | 1.0 | 1.0 | 1.0 | 1.0 | 1.0 | 1.0 | 1.0 | 1.0 |
| HIS | 0.25 | 0.25 | 0.25 | 0.25 | 0.25 | 0.25 | 0.25 | 0.25 |
| NBT | 1.5 | 1.5 | 1.5 | 1.5 | 1.5 | 1.5 | 1.5 | 1.5 |
| MgSt | 0.5 | 0.5 | 0.5 | 0.5 | 0.5 | 0.5 | 0.5 | 0.5 |
| Total layer 2 | 100 | 100 | 100 | 100 | 100 | 100 | 100 | 100 |

NBT = Nicotine bi-tartrate (nicotine content of 32.38% by weight)

The lozenges were prepared as described for example 1-8.

TABLE 4

Compositions of first and second layers.

| Raw material | Ex 25 | Ex 26 | Ex 27 | Ex 28 | Ex 29 | Ex 30 | Ex 31 | Ex 32 |
|---|---|---|---|---|---|---|---|---|
| | Content in weight percent of Layer 1 | | | | | | | |
| Mannitol | 95.85 | 93.95 | 92.05 | 90.15 | 97.75 | 97.75 | 97.75 | 97.75 |
| Buffer | 0.5 | 0.5 | 0.5 | 0.5 | 0.5 | 0.5 | 0.5 | 0.5 |
| Flavor | 1.0 | 1.0 | 1.0 | 1.0 | 1.0 | 1.0 | 1.0 | 1.0 |
| HIS | 0.25 | 0.25 | 0.25 | 0.25 | 0.25 | 0.25 | 0.25 | 0.25 |
| NPR | 1.9 | 3.8 | 5.7 | 7.6 | — | — | — | — |
| MgSt | 0.5 | 0.5 | 0.5 | 0.5 | 0.5 | 0.5 | 0.5 | 0.5 |
| Total layer 1 | 100 | 100 | 100 | 100 | 100 | 100 | 100 | 100 |
| Raw material | Content in weight percent of Layer 2 | | | | | | | |
| Mannitol | 88.75 | 88.75 | 88.75 | 88.75 | 87.75 | 86.75 | 85.75 | 83.75 |
| Superdisintegrant | 8 | 8 | 8 | 8 | 8 | 8 | 8 | 8 |
| Flavor | 1 | 1 | 1 | 1 | 1 | 1 | 1 | 1 |
| HIS | 0.25 | 0.25 | 0.25 | 0.25 | 0.25 | 0.25 | 0.25 | 0.25 |
| NBT | 1.5 | 1.5 | 1.5 | 1.5 | 1.5 | 1.5 | 1.5 | 1.5 |
| MgSt | 0.5 | 0.5 | 0.5 | 0.5 | 0.5 | 0.5 | 0.5 | 0.5 |
| Buffer | — | — | — | — | 1 | 2 | 3 | 5 |
| Total layer 2 | 100 | 100 | 100 | 100 | 100 | 100 | 100 | 100 |

NBT = Nicotine bi-tartrate (nicotine content of 32.38% by weight),
NPR = Nicotine Polacrilex Resin (nicotine content of 15% by weight)

Alternative ingredients as described in relation to examples 1-24 may also be applied for examples 25-32.

Examples 33-40

Different Sugar Alcohols 500 mg nicotine lozenges where made each with 350 mg first module and 150 mg second module.

The lozenges were prepared as described for example 1-8.

TABLE 5

Compositions of first and second layers.

| Raw material | Ex 33 | Ex 34 | Ex 35 | Ex 36 | Ex 37 | Ex 38 | Ex 39 | Ex 40 |
|---|---|---|---|---|---|---|---|---|
| | Content in weight percent of Layer 1 | | | | | | | |
| Mannitol | 97.75 | — | — | — | 50.00 | 50.00 | 50.00 | — |
| Isomalt | — | 97.75 | — | — | 47.75 | — | — | 50.00 |
| Sorbitol | — | — | 97.75 | — | — | 47.75 | — | 47.75 |
| Maltitol | — | — | — | 97.75 | — | — | 47.75 | — |
| Buffer | 0.5 | 0.5 | 0.5 | 0.5 | 0.5 | 0.5 | 0.5 | 0.5 |
| Flavor | 1.0 | 1.0 | 1.0 | 1.0 | 1.0 | 1.0 | 1.0 | 1.0 |
| HIS | 0.25 | 0.25 | 0.25 | 0.25 | 0.25 | 0.25 | 0.25 | 0.25 |
| MgSt | 0.5 | 0.5 | 0.5 | 0.5 | 0.5 | 0.5 | 0.5 | 0.5 |
| Total layer 1 | 100 | 100 | 100 | 100 | 100 | 100 | 100 | 100 |
| Raw material | Content in weight percent of Layer 2 | | | | | | | |
| Mannitol | 88.75 | 78.75 | 68.75 | 58.75 | 48.75 | 38.75 | — | 58.75 |
| Erythritol | — | 10 | 20 | 30 | 40 | 50 | 88.75 | — |
| Xylitol | — | — | — | — | — | — | — | 30 |
| Disintegrant | 8 | 8 | 8 | 8 | 8 | 8 | 8 | 8 |
| Flavor | 1 | 1 | 1 | 1 | 1 | 1 | 1 | 1 |

TABLE 5-continued

Compositions of first and second layers.

| | Ex | | | | | | | |
|---|---|---|---|---|---|---|---|---|
| | 33 | 34 | 35 | 36 | 37 | 38 | 39 | 40 |
| HIS | 0.25 | 0.25 | 0.25 | 0.25 | 0.25 | 0.25 | 0.25 | 0.25 |
| NBT | 1.5 | 1.5 | 1.5 | 1.5 | 1.5 | 1.5 | 1.5 | 1.5 |
| MgSt | 0.5 | 0.5 | 0.5 | 0.5 | 0.5 | 0.5 | 0.5 | 0.5 |
| Total layer 2 | 100 | 100 | 100 | 100 | 100 | 100 | 100 | 100 |

NBT = Nicotine bi-tartrate (nicotine content of 32.38% by weight)

Alternative ingredients as described in relation to examples 1-32 may also be applied for examples 33-40.

Examples 41-48

Examples 41-42 are 400 mg nicotine lozenges each made with 300 mg first module and 100 mg second module.

Examples 43-48 are 500 mg nicotine lozenges each made with 350 mg first module and 150 mg second module.

Subject to the above, the lozenges were prepared as described for example 1-8.

TABLE 6

Compositions of first and second layers.

| | Ex | | | | | | | |
|---|---|---|---|---|---|---|---|---|
| | 41 | 42 | 43 | 44 | 45 | 46 | 47 | 48 |
| Raw material | Content in weight percent of Layer 1 | | | | | | | |
| Mannitol | 93.3 | — | — | — | — | — | — | — |
| Isomalt | — | 93.3 | 98.20 | 98.20 | 98.20 | 98.20 | — | 96.06 |
| Sorbitol | — | — | — | — | — | — | 98.20 | 0 |
| HIS | 1.7 | 1.7 | 0.25 | 0.25 | 0.25 | 0.25 | 0.25 | 0.25 |
| Flavor | 4.0 | 4.0 | 1.05 | 1.05 | 1.05 | 1.05 | 1.05 | 1.05 |
| Xanthan gum | — | — | — | — | — | — | — | 2.14 |
| MgSt | 1.0 | 1.0 | 0.5 | 0.5 | 0.5 | 0.5 | 0.5 | 0.5 |
| Total layer 1 | 100 | 100 | 100 | 100 | 100 | 100 | 100 | 100 |
| Raw material | Content in weight percent of Layer 2 | | | | | | | |
| Mannitol | 75.00 | 75.00 | 95.25 | 46.42 | — | 46.08 | 95.25 | 95.25 |
| Erythritol | — | — | — | — | — | 49.07 | — | — |
| Pearlitol ® Flash | — | — | — | 48.83 | 95.25 | — | — | — |
| MCC | 5.00 | 5.00 | — | — | — | — | — | — |
| Superdisintegrant | 10.00 | 10.00 | — | — | — | — | — | — |
| Buffer | 5.00 | 5.00 | — | — | — | — | — | — |
| HIS | — | — | 0.25 | 0.25 | 0.25 | 0.25 | 0.25 | 0.25 |
| Flavor | — | — | 1.00 | 1.00 | 1.00 | 1.00 | 1.00 | 1.00 |
| MgSt | — | — | 0.50 | 0.50 | 0.50 | 0.60 | 0.50 | 0.50 |
| Sodium Stearyl Fumerate | 2.00 | 2.00 | — | — | — | — | — | — |
| NBT | 3.0 | 3.0 | 3.0 | 3.0 | 3.0 | 3.0 | 3.0 | 3.0 |
| Total layer 2 | 100 | 100 | 100 | 100 | 100 | 100 | 100 | 100 |

NBT = Nicotine bi-tartrate (nicotine content of 32.38% by weight)

Examples 41-42 show the use of MCC (microcrystalline cellulose) as a binder in layer 2 and sodium stearyl fumerate as a glidant in layer 2.

Alternative ingredients as described in relation to examples 1-40 may also be applied for examples 41-48.

Examples 49-56

Nicotine Sources and Ready to Use Systems 500 mg nicotine lozenges where made each with 350 mg first module and 150 mg second module.

The lozenges were prepared as described for example 1-8.

TABLE 7

Compositions of first and second layers.

| Raw material layer 1 | Ex 49 | Ex 50 | Ex 51 | Ex 52 | Ex 53 | Ex 54 | Ex 55 | Ex 56 |
|---|---|---|---|---|---|---|---|---|
| | Content in weight percent of Layer 1 | | | | | | | |
| Mannitol | 97.75 | 97.75 | 97.75 | 97.75 | 97.75 | 97.75 | 97.75 | 97.75 |
| Buffer | 0.5 | 0.5 | 0.5 | 0.5 | 0.5 | 0.5 | 0.5 | 0.5 |
| Flavor | 1 | 1 | 1 | 1 | 1 | 1 | 1 | 1 |
| HIS | 0.25 | 0.25 | 0.25 | 0.25 | 0.25 | 0.25 | 0.25 | 0.25 |
| MgSt | 0.5 | 0.5 | 0.5 | 0.5 | 0.5 | 0.5 | 0.5 | 0.5 |
| Total layer 1 | 100 | 100 | 100 | 100 | 100 | 100 | 100 | 100 |

| Raw material layer 2 | Ex 49 | Ex 50 | Ex 51 | Ex 52 | Ex 53 | Ex 54 | Ex 55 | Ex 56 |
|---|---|---|---|---|---|---|---|---|
| | Content in weight percent of Layer 2 | | | | | | | |
| Nicotine-calcium carbonate* | 3.0 | — | — | — | — | — | — | — |
| Nicotine-MCC* | — | 3.0 | — | — | — | — | — | — |
| Nicotine-soluble fiber* | — | — | 3.0 | — | — | — | — | — |
| Nicotine-sugar alcohol* | — | — | — | 3.0 | — | — | — | — |
| NBT | — | — | — | — | 3.0 | 3.0 | 3.0 | 3.0 |
| Mannitol | 79.7 | 79.7 | 79.7 | 79.7 | — | — | — | — |
| Ludiflash ® | — | — | — | — | 84.7 | — | — | — |
| SmartEX ® QD50 | — | — | — | — | — | 84.7 | — | — |
| F-Melt ® | — | — | — | — | — | — | 84.7 | — |
| ProSolv ® ODT G2 | — | — | — | — | — | — | — | 84.7 |
| Crospovidone | 5.0 | 5.0 | 5.0 | 5.0 | — | — | — | — |
| Flavor | 5.9 | 5.9 | 5.9 | 5.9 | 5.9 | 5.9 | 5.9 | 5.9 |
| HIS | 0.4 | 0.4 | 0.4 | 0.4 | 0.4 | 0.4 | 0.4 | 0.4 |
| Buffer | 5.0 | 5.0 | 5.0 | 5.0 | 5.0 | 5.0 | 5.0 | 5.0 |
| MgSt | 1.0 | 1.0 | 1.0 | 1.0 | 1.0 | 1.0 | 1.0 | 1.0 |
| Total | 100.0 | 100.0 | 100.0 | 100.0 | 100.0 | 100.0 | 100.0 | 100.0 |

NBT = Nicotine bi-tartrate (nicotine content of 32.38% by weight).
*free nicotine base sorbed onto carrier in a weight ratio of 1:2

Alternative ingredients as described in relation to examples 1-48 may also be applied for examples 49-56.

Examples 57-64

Sugar Alcohol Particle Size and Dissolution Modifiers

The lozenges were prepared as described for example 1-8.

TABLE 8

Compositions of first and second layers.

| Raw material layer 1 | Ex 57 | Ex 58 | Ex 59 | Ex 60 | Ex 61 | Ex 62 | Ex 63 | Ex 64 |
|---|---|---|---|---|---|---|---|---|
| | Content in weight percent of Layer 1 | | | | | | | |
| Mannitol DC 300 | 97.75 | — | — | 92.25 | 92.25 | 92.25 | 95.50 | 95.50 |

TABLE 8-continued

Compositions of first and second layers.

| | Ex | | | | | | | |
|---|---|---|---|---|---|---|---|---|
| | 57 | 58 | 59 | 60 | 61 | 62 | 63 | 64 |
| Mannitol 150 SD | — | 97.75 | — | — | — | — | — | — |
| Mannitol 200 SD | — | — | 97.75 | — | — | — | — | — |
| Sodium Alginate | — | — | — | 5.5 | — | — | — | 2.25 |
| Calcium polycarbophil | — | — | — | — | 5.5 | — | — | — |
| Xanthan gum | — | — | — | — | — | 5.5 | 2.25 | — |
| Buffer | 0.5 | 0.5 | 0.5 | 0.5 | 0.5 | 0.5 | 0.5 | 0.5 |
| Flavor | 1 | 1 | 1 | 1 | 1 | 1 | 1 | 1 |
| HIS | 0.25 | 0.25 | 0.25 | 0.25 | 0.25 | 0.25 | 0.25 | 0.25 |
| MgSt | 0.5 | 0.5 | 0.5 | 0.5 | 0.5 | 0.5 | 0.5 | 0.5 |
| Total layer 1 | 100 | 100 | 100 | 100 | 100 | 100 | 100 | 100 |

| Raw material layer 2 | Content in weight percent of Layer 2 | | | | | | | |
|---|---|---|---|---|---|---|---|---|
| Mannitol | 88.75 | 87.25 | 85.75 | 84.25 | 82.75 | 81.25 | 78.25 | 75.25 |
| Disintegrant | 8 | 8 | 8 | 8 | 8 | 8 | 8 | 8 |
| Flavor | 1 | 1 | 1 | 1 | 1 | 1 | 1 | 1 |
| HIS | 0.25 | 0.25 | 0.25 | 0.25 | 0.25 | 0.25 | 0.25 | 0.25 |
| NBT | 1.5 | 3.0 | 4.5 | 6.0 | 7.5 | 9 | 12.0 | 15.0 |
| MgSt | 0.5 | 0.5 | 0.5 | 0.5 | 0.5 | 0.5 | 0.5 | 0.5 |
| Total layer 2 | 100 | 100 | 100 | 100 | 100 | 100 | 100 | 100 |

NBT = Nicotine bi-tartrate (nicotine content of 32.38% by weight).

Mannitol DC 300, Mannitol 150 SD, and Mannitol 200 SD are commercially available from Roquette and have different average particle sizes.

Alternative ingredients as described in relation to examples 1-56 may also be applied for examples 57-64.

Example 65

Evaluations—First Layer of Examples 43 and 47

Examples 43 and 47 were each manufactured in three versions, where the applied pressure used to press the first layer was 10 kN, 20 kN, and 30 kN (single punch device with a punch diameter of 10.0 mm), respectively. Five nicotine lozenges were made for each of these versions.

For each version of the lozenges 43 and 47, a breaking point test, a fragility test and a dissolution time measurement were performed on the first layer.

For measuring breaking point, a PTB 311 from Pharma Test was used.

The fragility test involved evaluating the number of crushed layers produced. When all five were intact, a "pass" grade was assigned, whereas one or more crushed layers is indicated by the number of crushed layers. Alternatively, friability could be used as a measure of the fragility.

To test dissolution time, the following method was used. 15 mL of 0.02 M potassium dihydrogen phosphate-buffer (pH adjusted to 7.4) is added to 50 mL of water in a measuring tube with a screw cap. The lozenge is inserted in the measuring tube and the screw cap is fastened. The measuring tube is fixated horizontally. The measuring tube is vibrated at about 110 RPM such that the lozenge can move back and forth in the measuring tube. The measuring tube is vibrated until the lozenge or module thereof in question is completely dissolved and the time of vibration is noted as the dissolution time.

TABLE 9

Fragility test indicates number of lozenges crushed during testing, or "pass" when no lozenges were crushed.

| Test | Compression force [kN] | Example 43 Layer 1 (lozenge) | Example 47 Layer 1 (lozenge) | Example 48 Layer 1 (lozenge) |
|---|---|---|---|---|
| Breaking point | 10 | 193N | 237N | 195N |
| | 20 | 232N | 239N | 229N |
| | 30 | 205N | 249N | 220N |
| Fragility | 10 | Pass | Pass | Pass |
| | 20 | Pass | Pass | Pass |
| | 30 | Pass | Pass | Pass |
| Dissolution time | 10 | 9 min, 7 sec | 6 min, 12 sec | 12 min 10 sec |
| | 20 | 9 min, 41 sec | 6 min, 38 sec | 13 min 32 sec |
| | 30 | 9 min, 50 sec | 7 min, 05 sec | 16 min 0 sec |

As can be seen from table 9, the breaking points test reveals that example 47 having a first layer based on sorbitol as the sugar alcohol gives a higher breaking point that example 43 having a first layer based on isomalt as the sugar alcohol. Example 43 showed that the version pressed with 30 kN actually had a lower breaking point than that pressed with 20 kN, indicating that 30 kN pressing force would be too high and that the direct compressibility of the sugar alcohol (isomalt) is compromised.

Also, it is observed that all tested layers scored a pass in the fragility test, meaning that none of the five of each version was evaluated to be fragile or crushed during manufacturing.

Further, dissolution time test showed that sorbitol-based example 47 generally dissolved faster than isomalt-based example 43. Further, a higher pressing forces resulted in longer dissolution time.

Finally, example 48 is compared with example 43. Example 48 is somewhat similar to example 43, but additionally comprising xanthan gum. As seen from table 9, addition of xanthan gum did not noticeably affect breaking point test or fragility test, however, the dissolution time was significantly increased from around 9-10 minutes for example 43 to about 12-16 minutes for example 48, demonstrating effect of xanthan gum to delay dissolution and hence release of its constituents, such as sugar alcohol, flavor, nicotine (if any) etc. While obtaining the above, no compromising of the masking effect of the first layer was observed.

Example 66

Evaluation—Second Layer of Examples 43, 44, 45, and 46

Examples 43, 44 and 45 were each manufactured in three versions, where the applied pressure used to press the first layer was 10 kN, 20 kN, and 30 kN, respectively. Five nicotine lozenges were made for each of these versions.

For each version of the lozenges 43, 44, and 45, a breaking point test, a fragility test and a dissolution time measurement were performed on the second layer.

First, looking at examples 43-45, table 10 shows that the breaking point of the second layers of the produced lozenged generally increases with increasing compressing force from 10 kN to 30 kN.

Nevertheless, table 10 also shows that fragility may be a concern. It is noted that example 43 performed reasonably well with only 1 lozenge breaking during testing.

Table 10 also shows that a trade off may exist between applying a sufficient compression force to obtain a non-fragile second layer, but that increasing the compression force also impacts the dissolution time.

Further, it is noted that using disintegrant in the second layer (examples 44-45) resulted in decreased dissolution time over no disintegrant in the second layer (example 43), and further that increasing the amount of disintegrant as in example 45 over example 44 lead to a further decrease in dissolution time.

Taking also example 46 into account, it is noted that while very fragile second modules were produced, a rather short dissolution time was measured. It is noted that when evaluating the particle size distribution of the mannitol used in examples 43-44 and 46, the Pearlitol® Flash used in example 44-45, and the erythritol used in example 46, the Pearlitol® Flash showed the smallest particles sized, followed by the mannitol, whereas the erythritol applied (a non-DC grade of erythritol) had significantly larger particles. Using the non-DC grade erythritol with larger particles resulted in relatively fast dissolution times.

Example 67

Evaluation of Example 45

Example 45 lozenges where made with the compression forces indicated in table 11.

TABLE 10

Fragility test indicates number of lozenges crushed during testing, or "pass" when no lozenges were crushed.

| Test | Compr. force [kN] | Example 43 Layer 2 (FDT) | Example 44 Layer 2 (FDT) | Example 45 Layer 2 (FDT) | Example 46 Layer 2 (FDT) |
|---|---|---|---|---|---|
| Breaking point | 10 | 50N | 46N | 43N | 13N |
|  | 20 | N/A | 55N | 62N | 20N |
|  | 30 | N/A | 72N | 73N | 11N |
| Fragility | 10 | 1 lozenge | 1 lozenge | 1 lozenge | 5 lozenges |
|  | 20 | N/A | Pass | Pass | 5 lozenges |
|  | 30 | N/A | Pass | Pass | 5 lozenges |
| Dissolution | 10 | 2 min, 20 sec | 50 sec | 50 sec | 35 sec |
|  | 20 | N/A | 1 min, 15 sec | 50 sec | 1 min 40 sec |
|  | 30 | N/A | 2 min, 08 sec | 1 min 17 sec | 2 min 50 sec |

TABLE 11

| Compression force Layer 1 | Compression force Layer 2 | Fraglility | Dissolution time |
|---|---|---|---|
| 10 kN | 5 kN | Fragile. Decapping layer 1 from layer 2 | N/A |
| 5 kN | 5 kN | Not fragile. No decapping | layer 1: 5 min 20 sec layer 2: 1 min |
| 8 kN | 5 kN | Not fragile. No decapping | layer 1: 6 min layer 2: 1 min |
| 5 kN | 2 kN | Not fragile. No decapping | Layer 1: 5 min 30 sec Layer 2: 45 sec. |

Table 11 shows that it is possible to compress layer 1 with a compression force that is higher than the compression force applied to layer 2, while still obtaining nicotine lozenges that are not too fragile. It is noted, however, that decapping of layer 2 from layer 1 may be avoided if the compression force applied to layer 1 is not too high. Furthermore, the measured dissolution times were fully acceptable, particularly since the second layers dissolved within 1 minute, whereas the first layers all took more than 5 minutes to dissolve.

Example 68

General Evaluation

The lozenges of example 41-43 and 45 were evaluated by a panel of 7 trained assessors.

The evaluated lozenges generally were evaluated to give an improved release over conventional nicotine lozenges, e.g. with respect to nicotine release and prolonged masking.

The invention claimed is:

1. A water-dissolvable compressed oral nicotine lozenge comprising a first module and a second module,
    the first and the second modules being fused by compression,
    the first and second modules being formed by a plurality of compressed particles,
    the first module being a lozenge module comprising at least one sugar alcohol in an amount of at least 50% by weight of the first module, wherein the at least one sugar alcohol of the first module comprises at least one sugar alcohol selected from the group of xylitol, maltitol, mannitol, erythritol, isomalt, sorbitol, lactitol or any combination thereof, and
    the second module being a fast disintegrating tablet-module comprising at least one sugar alcohol in an amount of at least 50% by weight of the second module, superdisintegrant in an amount of between 1 and 14% by weight of the second module, and nicotine, wherein the at least one sugar alcohol of the second module comprises at least one sugar alcohol selected from the group of xylitol, maltitol, mannitol, erythritol, isomalt, sorbitol, lactitol or any combination thereof,
    wherein the water-dissolvable compressed oral nicotine lozenge has a maximum total weight of 0.75 gram,
    wherein the first module is free of nicotine,
    wherein the first module comprises flavor, and
    wherein the superdisintegrant comprises cross-linked polyvinylpyrrolidone in an amount of between 1 and 14% by weight of the second module.

2. The water-dissolvable compressed oral nicotine lozenge according to claim 1, wherein the second module comprises nicotine in an amount of less than 5% by weight of the second module.

3. The water-dissolvable compressed oral nicotine lozenge according to claim 1, wherein the weight of the second module is between 50 mg and 250 mg.

4. The water-dissolvable compressed oral nicotine lozenge according to claim 1, wherein the water-dissolvable compressed oral nicotine lozenge comprises nicotine in an amount of at least 0.5 mg.

5. The water-dissolvable compressed oral nicotine lozenge according to claim 1, wherein the second module comprises a nicotine salt.

6. The water-dissolvable compressed oral nicotine lozenge according to claim 1, wherein the second module further comprises disintegrant.

7. The water-dissolvable compressed oral nicotine lozenge according to claim 1, wherein the second module further comprises disintegrant in the amount of between 1% and 25% by weight of the second module.

8. The water-dissolvable compressed oral nicotine lozenge according to claim 6, wherein the disintegrant comprises cross-linked polyvinylpyrrolidone.

9. The water-dissolvable compressed oral nicotine lozenge according to claim 1, wherein the average particle size of the particles applied for the compression of the first module is larger than the average particle size of the particles applied for the compression of the second module.

10. The water-dissolvable compressed oral nicotine lozenge according to claim 1, wherein the second module comprises 10% to 50% by weight of the lozenge.

11. The water-dissolvable compressed oral nicotine lozenge according to claim 1, wherein the water-dissolvable compressed oral nicotine lozenge has a maximum total weight of 0.5 gram.

12. The water-dissolvable compressed oral nicotine lozenge according to claim 1, wherein the second module comprises the at least one sugar alcohol in an amount of at least 60% by weight of the second module.

13. The water-dissolvable compressed oral nicotine lozenge according to claim 1, wherein the first module comprises the at least one sugar alcohol in an amount of at least 60% by weight of the first module.

14. The water-dissolvable compressed oral nicotine lozenge according to claim 1, wherein the water-dissolvable compressed oral nicotine lozenge is free of mono- and disaccharides.

15. The water-dissolvable compressed oral nicotine lozenge according to claim 1, wherein the water-dissolvable compressed oral nicotine lozenge comprises a pH regulating agent.

16. The water-dissolvable compressed oral nicotine lozenge according to claim 1, wherein the first module further comprises at least one mucoadhesive in the amount of 0.5 to 10% by weight of the first module.

17. A water-dissolvable compressed oral nicotine lozenge comprising a first module and a second module,
the first and the second modules being fused by compression,
the first and second modules being formed by a plurality of compressed particles,
the first module being a lozenge module comprising at least one sugar alcohol in an amount of at least 50% by weight of the first module and
the second module being a fast disintegrating tablet-module comprising at least one sugar alcohol in an amount of at least 50% by weight of the second module, disintegrant, and nicotine,
wherein the water-dissolvable compressed oral nicotine lozenge has a maximum total weight of 0.75 gram,
wherein the first module is free of nicotine, and
wherein the first module comprises flavor.

18. A water-dissolvable compressed oral nicotine lozenge comprising a first module and a second module,
the first and the second modules being fused by compression,
the first and second modules being formed by a plurality of compressed particles,
the first module being a lozenge module comprising at least one sugar alcohol in an amount of at least 50% by weight of the first module, wherein the at least one sugar alcohol of the first module comprises at least one sugar alcohol selected from the group of xylitol, maltitol, mannitol, erythritol, isomalt, sorbitol, lactitol or any combination thereof, and
the second module being a fast disintegrating tablet-module comprising at least one sugar alcohol in an amount of at least 50% by weight of the second module, superdisintegrant in an amount of between 1 and 14% by weight of the second module, and nicotine, wherein the at least one sugar alcohol of the second module comprises at least one sugar alcohol selected from the group of xylitol, maltitol, mannitol, erythritol, isomalt, sorbitol, lactitol or any combination thereof,
wherein the water-dissolvable compressed oral nicotine lozenge has a maximum total weight of 0.75 gram,
wherein the weight of the second module is between 50 mg and 150 mg,
wherein the first module is free of nicotine,
wherein the first module comprises flavor, and
wherein the superdisintegrant comprises cross-linked polyvinylpyrrolidone in an amount of between 1 and 14% by weight of the second module.

* * * * *